(12) United States Patent
Ragaru et al.

(10) Patent No.: US 7,932,429 B2
(45) Date of Patent: Apr. 26, 2011

(54) DEVICE DESIGNED FOR REGENERATING THE HUMAN DERMIS AND PROCESS FOR PRODUCING SAID DEVICE

(75) Inventors: Bernard Ragaru, Brignais (FR); Benjamin Herbage, Lyons (FR)

(73) Assignee: Symatese, Chaponost (FR)

( * ) Notice: Subject to any disclaimer, the term of this patent is extended or adjusted under 35 U.S.C. 154(b) by 1155 days.

(21) Appl. No.: 11/616,157

(22) Filed: Dec. 26, 2006

(65) Prior Publication Data

US 2008/0113572 A1 May 15, 2008

(30) Foreign Application Priority Data

Nov. 10, 2006 (FR) ...................................... 06 54824

(51) Int. Cl.
*A61F 13/00* (2006.01)
(52) U.S. Cl. .......................................... 602/41; 602/42

(58) Field of Classification Search ............... 602/41–54
See application file for complete search history.

(56) References Cited

U.S. PATENT DOCUMENTS

| 3,419,006 | A | * | 12/1968 | King ............................. 604/290 |
| 4,060,081 | A | * | 11/1977 | Yannas et al. ............... 623/15.12 |
| 4,556,056 | A | * | 12/1985 | Fischer et al. ................. 604/304 |
| 4,638,795 | A | * | 1/1987 | Richter et al. .................... 602/8 |
| 5,505,952 | A | * | 4/1996 | Jiang et al. .................... 424/423 |

* cited by examiner

*Primary Examiner* — Michael A. Brown
(74) *Attorney, Agent, or Firm* — Heslin Rothenberg Farley & Mesiti P.C.

(57) ABSTRACT

Device designed for regenerating the human dermis presented in the form of a multilayer complex combining an absorbable polymeric internal matrix able to induce the regeneration of the dermis by contact with muscle or subcutaneous tissue, an open-work textile mesh and a transparent external support wherein the open-work textile mesh is contained in the body of the transparent support.

20 Claims, 2 Drawing Sheets

DEVICE DESIGNED FOR REGENERATING THE HUMAN DERMIS AND PROCESS FOR PRODUCING SAID DEVICE

CROSS REFERENCE TO RELATED APPLICATIONS

This application claims priority of French Application No. 0654824 filed on Nov. 10, 2006, which application is hereby incorporated by reference herein, in its entirety.

BACKGROUND OF THE INVENTION

The subject of this invention is a device designed for regenerating the human dermis. It also concerns a process for producing such a device.

Human dermis regeneration using a collagen or equivalent matrix followed by an epidermal graft is one of the most commonly used techniques for skin reformation. Third-degree burns are one of the main indications for this technique. Dermal regeneration is also called for in plastic surgery for the treatment of keloids, retractile scars, scar plaques, hypertrophic scars, skin necrosis following rejection of a skin graft and nevus. Dermal regeneration is also called for after the excision of a skin tumor, for the treatment of chronic or acute wounds when the dermis needs to be regenerated and in traumatology for reconstructive surgery.

Document U.S. Pat. No. 4,060,081 describes a device for dermal regeneration of the type described in the invention, in the form of a multilayer complex combining, successively:
  an absorbable polymeric matrix designed to come into contact with muscle or subcutaneous tissue, depending on the indication;
  a textile mesh with unspecified characteristics, applied to the surface of the matrix, not in contact with the muscle or subcutaneous tissue;
  a permeable film used as a temporary skin substitute, applied in strips directly onto the textile mesh.

The complex is thus presented in the form of three separate layers, respectively:
  an absorbable polymeric matrix;
  a textile mesh;
  a transparent, permeable layer, in practice in the form of a silicone film.

When these multilayer complexes are used for dermal regeneration, notably in burn victims, the surgeon proceeds as follows.

Firstly, if necessary, the nonviable parts of the burnt dermis are excised to obtain viable underlying tissue.

Directly on the muscle, or depending on the case, on the subcutaneous tissue:
  the multilayer complex is positioned so that the absorbable polymeric matrix is in contact with the muscle or subcutaneous tissue;
  the device is then attached to the muscle or cutaneous tissue using staples or suture, to keep it from moving during the dermal regeneration phase and to keep the wound sealed;
  once the dermis has been regenerated, which may take approximately three weeks, the double transparent film/textile mesh layer is removed;
  then, in the last step, an epidermal graft is performed on the regenerated dermis.

One of the major disadvantages of the device described in document U.S. Pat. No. 4,060,081 is that there is a direct contact between the dermis that is being formed and the textile mesh. When the double permeable film/textile mesh layer is removed, two situations may occur.

In some cases, removing the film/textile mesh group can cause at least part of the reformed dermis to pull off due to colonization of the textile by the host cells. Bleeding is then possible, as well as irregularity in the dermis. The epidermal graft is thus performed on a non-homogenous dermis with risks of persistent skin defects after reconstruction.

In other cases, the film can come unattached from the mesh so that the mesh remains set in the dermis being formed. In this hypothesis, the epidermal graft will be performed on a dermis containing a useless, non-absorbable material with risks of losing skin functions in terms of suppleness, elasticity and esthetics due to the persistence of the textile structure.

Another disadvantage of the device in the prior art is that it causes the formation of tears in the transparent film and the collagen matrix during attachment with staples and during regeneration of the dermis. The tear in the collagen matrix then leaves a hole that will have to be filled by the formation of a tissue called "granulation tissue", which is a sign of poor dermal reconstruction.

A third disadvantage lies in that the permeable film, given how thin it is, can tear near the points of attachment under the effects of the patient's movement. In this case, the subcutaneous tissue or muscle is no longer isolated from the ambient air, providing an open door to a major risk of contamination.

A fourth disadvantage lies in that the textile mesh gives the device a certain degree of stiffness. It may no longer adapt to the wound being treated on certain parts of the body with pronounced relief such as the fingers or face. Contact between the polymeric material and the bed of the wound is indispensable for good dermal reconstruction.

Lastly, the transparency of the permeable film can be affected by the presence of the textile mesh. Transparency is indispensable for monitoring the wound and notably for verifying that there is no infection or hematoma which could lead to the failure of dermal regeneration. Transparency also makes it possible to verify the progress made in dermal regeneration in order to schedule the epidermal graft.

BRIEF SUMMARY OF THE INVENTION

To solve all of these problems, the Applicant has developed a new device in which the textile mesh is integrated into the body of the transparent layer.

The transparent layer thus reinforced ensures safe removal not only of the transparent film, but also of the textile material once the dermis is definitively formed, just before grafting the epidermis. Furthermore, the Applicant has performed experiments demonstrating that the layer reinforced in this way does not tend to allow the holes formed by the staples to expand, thus eliminating any risk of contamination or unsatisfactory reconstruction.

Moreover, the Applicant has observed that the transparency of the layer reinforced with the textile mesh is better than the transparency of the layer and the textile mesh superposed.

The subject of the invention is therefore a device designed for regenerating the human dermis, presented in the form of a multilayer complex combining an internal, absorbable, colonizable polymeric matrix able to induce the regeneration of the dermis by contact with muscle or subcutaneous tissue, an open-work textile mesh and a transparent external support.

This device is characterized in that the open-work textile mesh is contained in the body of the transparent support thus constituting a reinforced transparent support.

By the expression "open-work textile mesh" we mean an open-work textile, whether woven, knit or non-woven.

To encourage interlinking of the reinforced transparent support, through the textile material, with the absorbable polymeric matrix, the device includes an adhesive layer between said support and the matrix, advantageously a silicone glue.

In practice, the absorbable polymeric material may be constituted of the collagen, polysaccharides (cellulose, alginate, agarose, chitosan), mucopolysaccharides (hyaluronic acid, chondroitin sulfate, heparin), glycoproteins (fibronectin, laminin, chondronectin), structural proteins (elastin or gelatin, for example) or absorbable synthetic polymers (polylactic, glycolics, etc.), alone or in combination. Other compounds may be added to the absorbable polymeric material, such as growth factors, antiseptics or antibiotics. It is known that the polymeric material may be crosslinked before being applied on the transparent support, depending on its nature. In practice, for the collagen, the crosslinking agent is glutaraldehyde, formaldehyde or N-hydroxysuccinimide, 1-ethyl-3-(3-dimethylaminopropyl)carbodiimide, a polysaccharide functionalized to react with the collagen. Crosslinking can also be achieved by physical treatment such as vacuum heat treatment or irradiation.

If the material is made of collagen, it will be a native collagen, fibrous collagen, atelocollagen or partially or totally denatured collagen.

In an advantageous embodiment, the absorbable polymeric material is exclusively constituted of collagen which is crosslinked before combining with the reinforced transparent support.

As for the open-work textile mesh, it must be sufficiently dense to provide effective reinforcement for the support, and consequently to avoid any risks of tearing at the contact point with the staples, while not affecting the transparency of the support, which is indispensable for the surgeon to be able to view the formation of the dermis, and its conformability, which is indispensable for its adaptation to the site being treated.

In practice, the density of the textile mesh is between 0.6 and 60 g/m$^2$, advantageously between 15 and 20 g/m$^2$.

According to another characteristic, the thread constituting the mesh has a dtex value between 10 and 30, advantageously between 20 and 25 dtex.

Furthermore, according to another characteristic, the mesh contains between 3 and 100, advantageously between 10 and 60 threads, and as many picks per centimeter.

In practice, the material constituting the textile mesh is made of synthetic fibers (polyester or polypropylene) or natural fibers (silk or cellulose), or cotton, in the form of single- or multi-strand thread.

As for the transparent support, it advantageously has permeability to water vapor, identical to that of the epidermis. In practice, it preferably comes in the form of a film of silicone, polyurethane (PU), or polyolefin (polyethylene (PE), polyethylene terephtalate copolyester (PETG), polyvinyl chloride (PVC)), transparent and non-absorbable for the time it takes for dermal reconstruction.

To obtain a transparent support in which the textile mesh is laid out regularly, i.e. the distance between said mesh and one or the other surface of the support is constant, the transparent support comes in the form of a sandwich comprising two silicone films applied to the two sides of the textile mesh.

In practice, the thickness of the reinforced transparent support is between 20 and 1,000 µm, advantageously between 200 and 300 µm.

The invention also concerns the production process for the aforementioned device.

According to this procedure:
an adhesive layer is sprayed onto the surface of a transparent support with an open-work textile mesh in its body,
the absorbable polymeric matrix, possibly crosslinked, is applied to the coated surface of the transparent support.

In practice, the transparent support is formed by applying two silicone films to the two sides of the textile mesh. As is known by people skilled in the art, the films can be interlinked by thermofusion or hot or cold pressing, possibly followed by heat treatment. The presence of the textile mesh in the support also provides a perfectly flat, non-deformed surface which can receive the sprayed layer of glue.

The absorbable polymer matrix is obtained from a collagen or other materials alone or in a mixture, as described previously.

In a particular embodiment, the absorbable matrix is constituted of 100% collagen.

In practice, the collagen is crosslinked and forms a dry, porous structure applied directly to the surface of the reinforced transparent layer in the form of a film.

The device thus obtained may be cut and then conditioned before being sterilized.

The invention also concerns a method for dermal regeneration consisting in:
first, if necessary, excising nonviable or scar parts of the dermis,
applying the device in the invention to the subcutaneous tissue or muscle, so that the absorbable polymeric matrix is in contact with said muscle or subcutaneous tissue,
attaching said device onto the muscle or skin tissue using means of attachment such as stapling or suture,
once the dermis has been regenerated, removing the means of attachment, followed by the reinforced transparent support,
grafting the epidermis by autograft, keratinocyte sheet obtained by culture, keratinocyte spray or any other epidermal regeneration technique.

In practice, before applying the device, it is hydrated.

BRIEF DESCRIPTION OF THE DRAWING FIGURES

The invention and the resulting advantages will be made clear by the attached example of embodiment, backed up by the appended figures.

DETAILED DESCRIPTION

Figure 1:
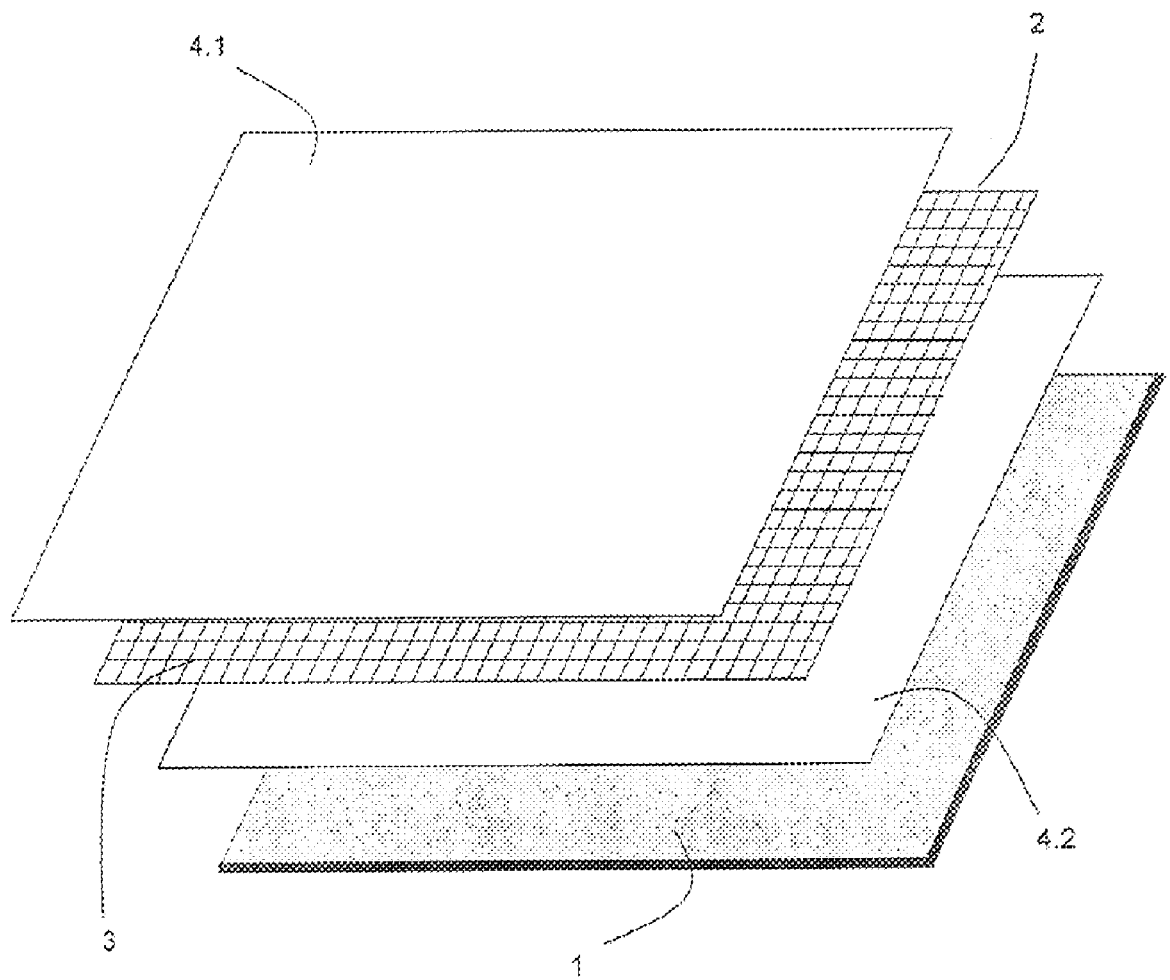
FIG. 1 is a schematic breakdown representation of the device in the invention.

As can be seen in FIG. 1, the device in the invention includes a first layer in the form of an absorbable polymeric matrix (1) constituted, in practice, of 100% collagen.

The initial collagen is native bovine dermal collagen, notably from calves, ground and then transformed into a gel before being lyophilized, then crosslinked with glutaraldehyde. The substance formed is in the form of a dry film which can be glued directly onto the reinforced transparent support. Preferably, the excess crosslinking agent is eliminated by washing or chemical reduction.

As can be seen in FIG. 1, the reinforced transparent support (2) includes a textile mesh (3) constituted of single-strand polyester threads whose texture corresponds to 36 threads and 36 picks per centimeter, while the density is 17 g/m$^2$.

This textile mesh (3) is sandwiched between two silicone films (4.1, 4.2), each with a thickness of approximately 100 µm.

In practice, the two silicone films are first applied to both surfaces of the textile mesh to form the reinforced transparent support. Interlinking of the whole is achieved by cold pressing followed by heat treatment. A silicone glue is then applied by spray or another coating technique to one of the surfaces of this layer, and then the previously prepared collagen matrix is applied.

Figure 2:
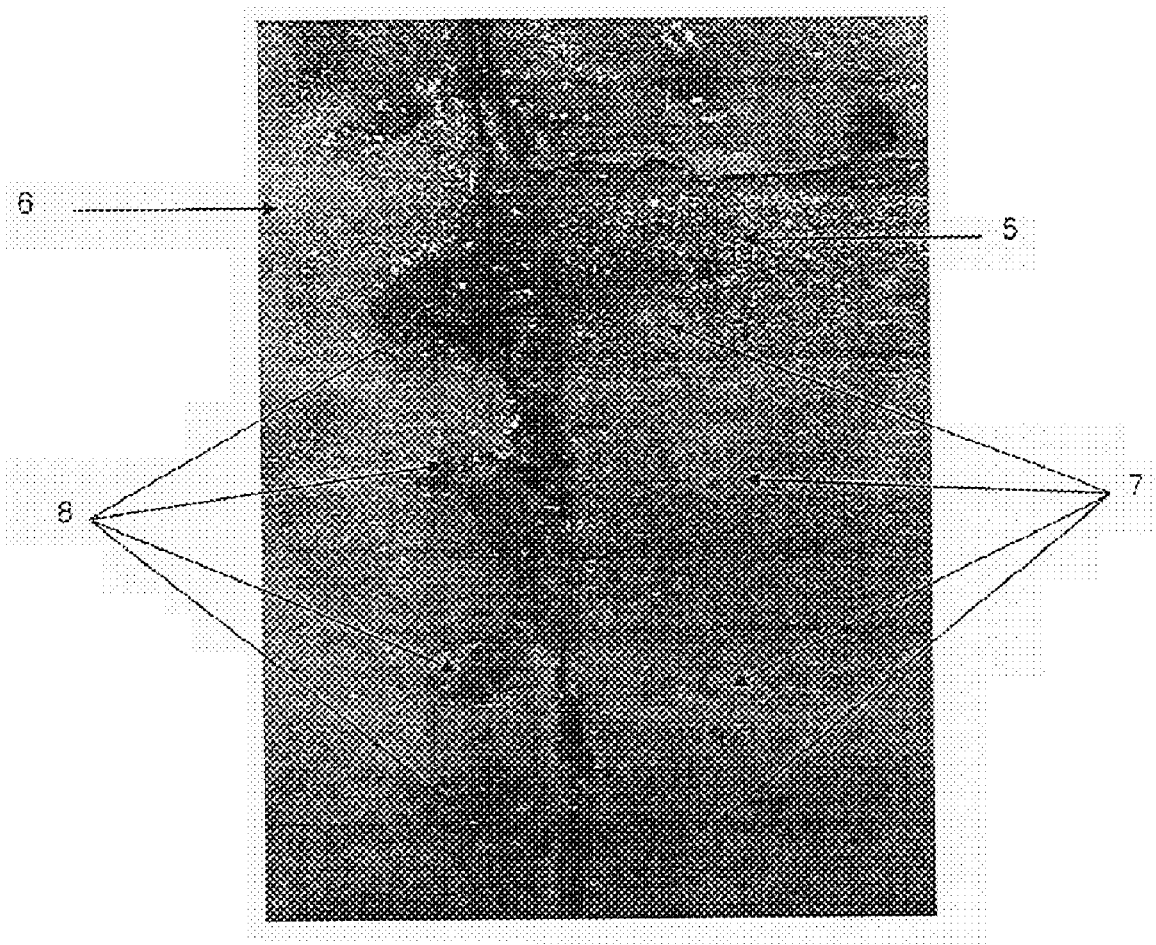
FIG. 2 is a photograph of the dermal reconstruction achieved with the device in the invention compared with that of a commercially available device.

FIG. 2 is a photograph of dermal reconstruction (just before the epidermal graft) achieved with the device of the invention (shown on the right-hand part [5] of the photograph) applied to the back of a patient initially burnt to the $3^{rd}$ degree and presenting a scar plaque that was excised. The substance was applied directly to the muscle and compared with INTEGRA® DRT (shown on the left-hand part [6] of the photograph).

In practice, after having excised the rest of the dermis, the surgeon applies the device so that the surface with the collagen is in contact with the muscle. The size of the device is chosen in relation to the size of the burn. Once the device has been applied, it is then stapled to the adjacent skin tissue or to another device of the same type. Once the dermis has been formed, the device is removed as already explained, by pulling off the reinforced support alone. A fine dermo-epidermal graft is then performed on the regenerated dermis.

FIG. 2 represents the dermis reconstructed with the device after three weeks. As can be seen in this photograph, the dermis reconstituted with the INTEGRA® DRT device presents granulation tissue growths at the staple points (8) indicating poor dermal regeneration. These growths are the result of the holes formed by the staples in the INTEGRA DRT, which expanded during the neodermal formation period.

On the other hand, the device of the invention did not tear around the holes formed by the staples, thanks to the presence of the textile mesh in the body of the transparent layer. Consequently, the dermis reconstituted with the device of the invention shows no granulation tissue growth at the stapling points (7).

The presence of the textile mesh inside the transparent layer also totally avoids colonization of the textile by the neodermis; the surface of the neodermis after removal of the transparent layer is therefore smooth and free of bleeding. The transparent layer was able to be removed without any partial excision of the neoformed dermis.

The invention and the resulting advantages are made clear in the above description. We can see that the resistance of the device in the invention during the formation of the dermis, thanks to the presence of the open-work mesh in the body of the film, ensured:

The absence of contamination;
The lack of formation of granulation tissue at the attachment points;
The absence of excision of the neoformed dermis upon removal of the transparent layer and the textile mesh;
Better transparency.

The invention claimed is:

1. Device for dermal regeneration comprising a multilayer complex combining an absorbable polymeric matrix able to induce the regeneration of dermis by contact with muscle or subcutaneous tissue, an open-work textile mesh and a transparent external support wherein the open-work textile mesh is contained in a body of the transparent support.

2. Device as claimed in claim 1, wherein the absorbable polymeric matrix is exclusively constituted of crosslinked collagen.

3. Device as claimed in claim 1, wherein density of the textile mesh is between 0.6 and 60 g/m².

4. Device as claimed in claim 1, wherein thread constituting the textile mesh has a dtex value between 10 and 30.

5. Device as claimed in claim 1, wherein the textile mesh contains between 3 and 100 threads per centimeter, and as many picks per centimeter.

6. Device as claimed in claim 1, wherein material constituting the textile mesh is polyester, polypropylene, or cotton, in the form of a single- or multi-strand thread.

7. Device as claimed in claim 1, wherein the transparent support is in the form of a sandwich containing two silicone films applied to two opposite sides of the textile mesh.

8. Device as claimed in claim 7, wherein thickness of the transparent support is between 20 and 1,000 µm.

9. Device as claimed in claim 1, further comprising an adhesive layer between the transparent support and the polymeric matrix.

10. Production process for the device of claim 1, wherein:
an adhesive layer is applied to a surface of a reinforced transparent support having an internal open-work textile mesh, and
the absorbable polymeric matrix is applied to the adhesive layer.

11. Process as claimed in claim 10, wherein the reinforced transparent support is formed by application of two silicone films to two opposite sides of the textile mesh.

12. Process as claimed in claim 10, further comprising conditioning and then sterilizing the device.

13. Device as claimed in claim 3, wherein the density of the textile mesh is between 15 and 20 g/m².

14. Device as claimed in claim 4, wherein the thread constituting the textile mesh has a dtex value between 20 and 25.

15. Device as claimed in claim 5, wherein the textile mesh contains between 10 and 60 threads per centimeter.

16. Device as claimed in claim 8, wherein the thickness of the transparent support is between 200 and 300 µm.

17. A method for skin reformation comprising:
applying the device of claim 1 to muscle or subcutaneous tissue so that the absorbable polymeric matrix is in contact with said muscle or subcutaneous tissue;
attaching the device onto the muscle or subcutaneous tissue in order to keep the device from moving during regeneration of dermis;
once the dermis has been regenerated, removing the transparent support; and
grafting epidermis to the regenerated dermis.

18. The method as claimed in claim 17, wherein the device is attached to the muscle or subcutaneous tissues using staples, sutures or other attachment means, and further comprising the step, after the dermis has been regenerated, of removing said staples, sutures or other attachment means prior to removing the transparent support.

19. The method of claim 18, further comprising excising non-viable or scar parts of the dermis prior to applying the device.

20. The method as claimed in claim 17, wherein said grafting is accomplished by autograft, keratinocyte sheet obtained by culture, keratinocyte spray or other epidermal regeneration technique.

* * * * *